United States Patent
Chou et al.

(10) Patent No.: US 7,067,343 B2
(45) Date of Patent: Jun. 27, 2006

(54) ISFETS FABRICATION METHOD

(75) Inventors: Jung-Chuan Chou, Yunlin Hsien (TW); Zhi Jie Chen, Hsinchu (TW); Shih I Liu, Kaohsiung (TW)

(73) Assignee: National Yunlin University of Science and Technology, Yunlin Hsien (TW)

( * ) Notice: Subject to any disclaimer, the term of this patent is extended or adjusted under 35 U.S.C. 154(b) by 9 days.

(21) Appl. No.: 11/006,094

(22) Filed: Dec. 7, 2004

(65) Prior Publication Data

US 2006/0046375 A1    Mar. 2, 2006

(30) Foreign Application Priority Data

Aug. 30, 2004    (TW) .............................. 93126052 A

(51) Int. Cl.
*H01L 21/00*    (2006.01)

(52) U.S. Cl. .................. 438/49; 204/419; 204/420

(58) Field of Classification Search .................. 438/49; 204/419, 420
See application file for complete search history.

(56) References Cited

U.S. PATENT DOCUMENTS

| | | | |
|---|---|---|---|
| 4,397,714 A | 8/1983 | Janata et al. ................... 204/1 |
| 4,641,084 A | 2/1987 | Komatsu ................... 324/71.5 |
| 5,240,586 A * | 8/1993 | Moore et al. ............... 204/418 |
| 5,309,085 A | 5/1994 | Sohn ........................ 324/71.5 |
| 5,384,028 A | 1/1995 | Ito ............................. 204/403 |
| 5,911,873 A | 6/1999 | McCarron et al. .......... 205/789 |
| 5,925,318 A | 7/1999 | Kruzel et al. .................. 422/56 |
| 6,218,208 B1 | 4/2001 | Chou et al. ................... 438/49 |
| 6,251,246 B1 | 6/2001 | Chan .......................... 204/418 |
| 6,326,215 B1 | 12/2001 | Keen .......................... 436/518 |
| 6,409,909 B1 | 6/2002 | Spichiger-Keller et al. ...... 205/777.5 |

* cited by examiner

*Primary Examiner*—George Fourson
*Assistant Examiner*—Julio J. Maldonado
(74) *Attorney, Agent, or Firm*—Thomas, Kayden, Horstemeyer & Risley

(57) ABSTRACT

Methods for fabricating ion sensitive field effect transistors (ISFETs) with $SnO_2$ extended gates. A $SnO_2$ detection film is formed on a substrate by sol-gel technology to serve as an extended gate. The $SnO_2$ detection film is electrically connected to a conductive wire, and an insulating layer is formed on the surface of the ISFET but part of the $SnO_2$ detection film and the conductive wire are left exposed. The exposed conductive wire is electrically connected to a gate terminal of a MOS transistor.

13 Claims, 4 Drawing Sheets

ISFETS FABRICATION METHOD

BACKGROUND

The invention relates to ion sensitive field effect transistors (ISFETs), and more particularly, to methods for fabricating $SnO_2$ extended gate ISFETs.

The ion sensitive field effect transistor (ISFET) was presented by Piet Bergveld in 1970. An ISFET with reference electrode is similar to Metal-Oxide-Semiconductor Field Effect Transistor (MOSFET), except that the ISFET has exposed the gate insulator to measure a selected ion concentration in electrolyte. When the pH-ISFET is immersed in an aqueous solution, a surface potential is induced at the surface of the detection membrane of the pH-ISFET. However, the surface potential at the sensing membrane will affect the carrier concentration within the inversion layer of the semiconductor, due to the gate dielectric layer being extremely thin. Thus, the current, which flows through the channel, is adjusted. Furthermore, the surface potential is related to the hydrogen ion activity within the aqueous solution. As the pH values change, different surface potentials are induced at the detection membrane, leading to different channel currents. Thus, the pH-ISFET can be used to detect the pH values of solution.

Further, the extended gate field effect transistor (EGFET) structure was presented by J. V. D. Spiegel et al, in which the detection film is extended from the gate terminal of the field effect transistor by a conductive line. Thus, only the detection film requires immersion in a testing solution, without the field effect transistor.

A variety of materials are known to be capable of serving as ISFET detection film, such as, $Al_2O_3$, $Si_3N_4$, a-$WO_3$, a-C:H, and a-Si:H, etc. The manufacture of detection films is typically accomplished by deposition, such as, sputtering or plasma enhanced chemical vapor deposition (PECVD). Thus, the cost is relatively high and the time required for thin film fabrication is excessive.

Thus, an easily fabricated, low cost ISFET and the detection film thereof, eliminating packaging problems, are desirable.

SUMMARY

ISFET fabrication methods are provided. In an exemplary embodiment of a fabrication method for ISFETs with $SnO_2$ extended gates, wherein a $SnO_2$ detection film is formed on a substrate by sol-gel technology to serve as an extended gate. The $SnO_2$ detection film is then electrically connected with a conductive wire. An insulating layer is then formed on the surface of the ISFET but leaving part of the $SnO_2$ detection film and part of the conductive wire exposed. The exposed conductive wire is electrically connected to a gate terminal of a MOS transistor.

In some embodiments of a detection circuit, a current mirror provides a reference current, and a first operational amplifier comprises a non-inversion input terminal coupled to the reference current and an inversion input terminal coupled to a drain terminal of the ISFET. A first resistor comprises a first end coupled to the non-inversion input terminal of the first operational amplifier, and a second end. A second operational amplifier comprises a non-inversion input terminal coupled to a source terminal of the ISFET, and an inversion input terminal coupled to the second end of the first resistor. A drain-source voltage detection module is coupled to the source terminal of the ISFET, and a drain-source current detection module is coupled to the source terminal of the ISFET.

In some embodiments of a read circuit, a detection circuit detects the drain-source voltage and a drain-source current of the ISFET. A processing unit is coupled to the detection circuit to determine a pH value of an unknown solution according to the detected drain-source voltage and the detected drain-source current. A liquid crystal display is coupled to the processing unit to display the determined pH value.

DESCRIPTION OF THE DRAWINGS

The invention can be more fully understood by the subsequent detailed description and examples with reference made to the accompanying drawings, wherein.

DETAILED DESCRIPTION

FIGS. 1A~1D are flowcharts illustrating an embodiment of a $SnO_2$ extended gate ISFET fabrication method.

Figure 1A:
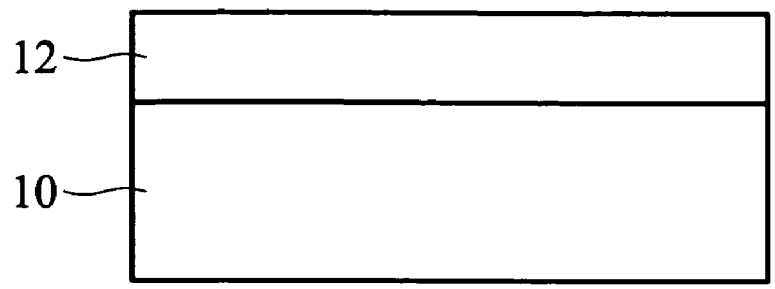
FIGS. 1A~1D are flowcharts illustrating an embodiment of an ISFET fabrication method.

A substrate is cut into squares of 8 cm×8 cm and rinsed with propyl alcohol, isopropanol and deionized water (DI water) respectively for 20 minutes. A $SnO_2$ detection film 12 is then formed on the substrate 10 by sol-gel technology to serve as an extended gate, as shown in FIG. 1A.

In the step of forming $SnO_2$ detection film 12, $SnCl_2$ powder ($SnCl_2 \cdot 2H_2O$) is dissolved by ethanol to prepare a mixed solution with a concentration of 0.37M. The mixed solution is then placed at room temperature for a first predetermined duration, for example 3 days, to form a light yellow color mixed solution. The light yellow color mixed solution is coated on the rinsed substrate 10, and the substrate 10 is dried at 350° C. in an oven for 1 hour to form the $SnO_2$ detection film 12, and then cooled to room temperature.

Figure 1B:
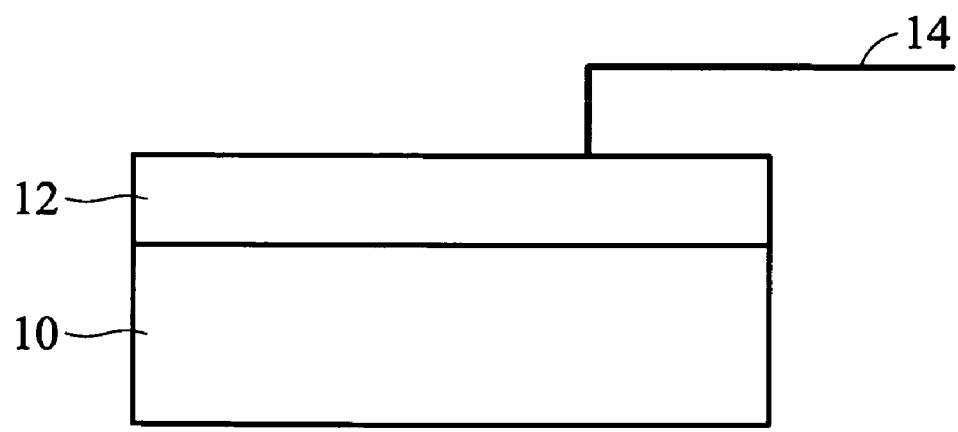

The substrate 10 with the $SnO_2$ detection film 12 is cut into squares of 1.5 cm×1.5 cm and washed in deionized water of an ultrasonic oscillator. One end of an aluminum conductive wire 14 is bonded to the $SnO_2$ detection film 12 by silver paste and dried at 120° C. in an oven for 10 minutes, and then cooled to room temperature, as shown in FIG. 1B.

Figure 1C:
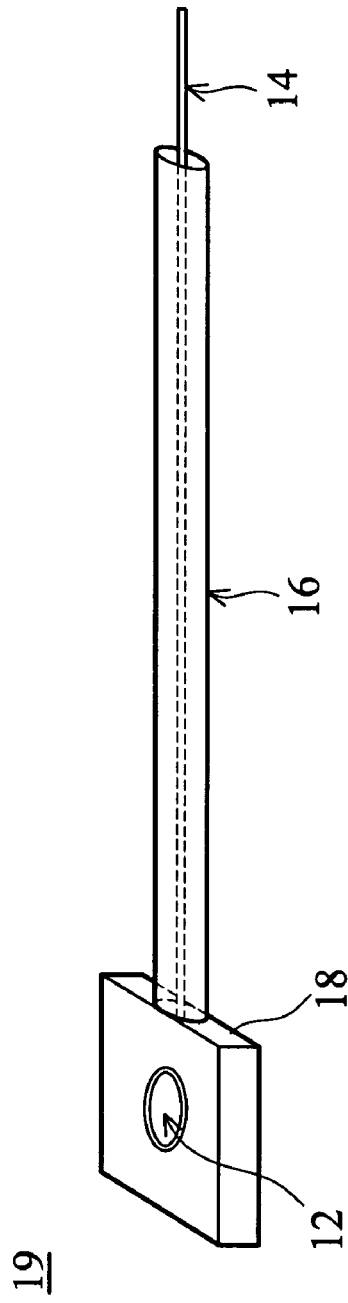
Figure 1D:
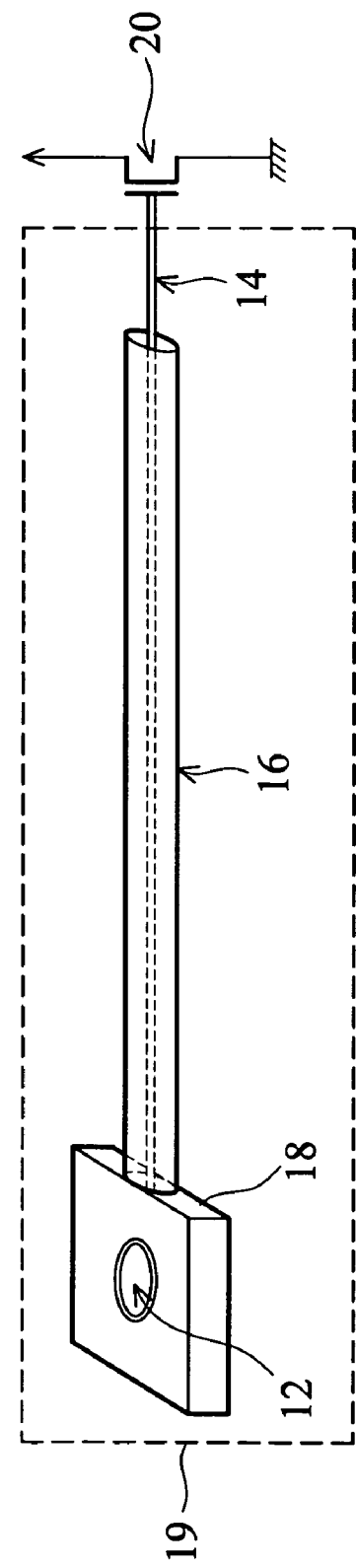

The aluminum conductive wire 108 is installed through a capillary 16, and the $SnO_2$ detection film 12, the substrate 10 and the capillary 16 are fixed by an insulating layer 18 comprising epoxy resin and dried at 120° C. in an oven for 20 minutes. The $SnO_2$ detection film 12 and the substrate 10 are then packaged with epoxy resin but an area of 2 mm×2 mm is kept to serve as a sensing window. The sensing portion 19 is obtained as shown in FIG. 1C.

Finally, the remaining end of the aluminum conductive wire 14 is electrically connected to a gate of a MOSFET 20, and the ISFET 100 with a $SnO_2$ detection film 12 is completed.

Figure 2A:
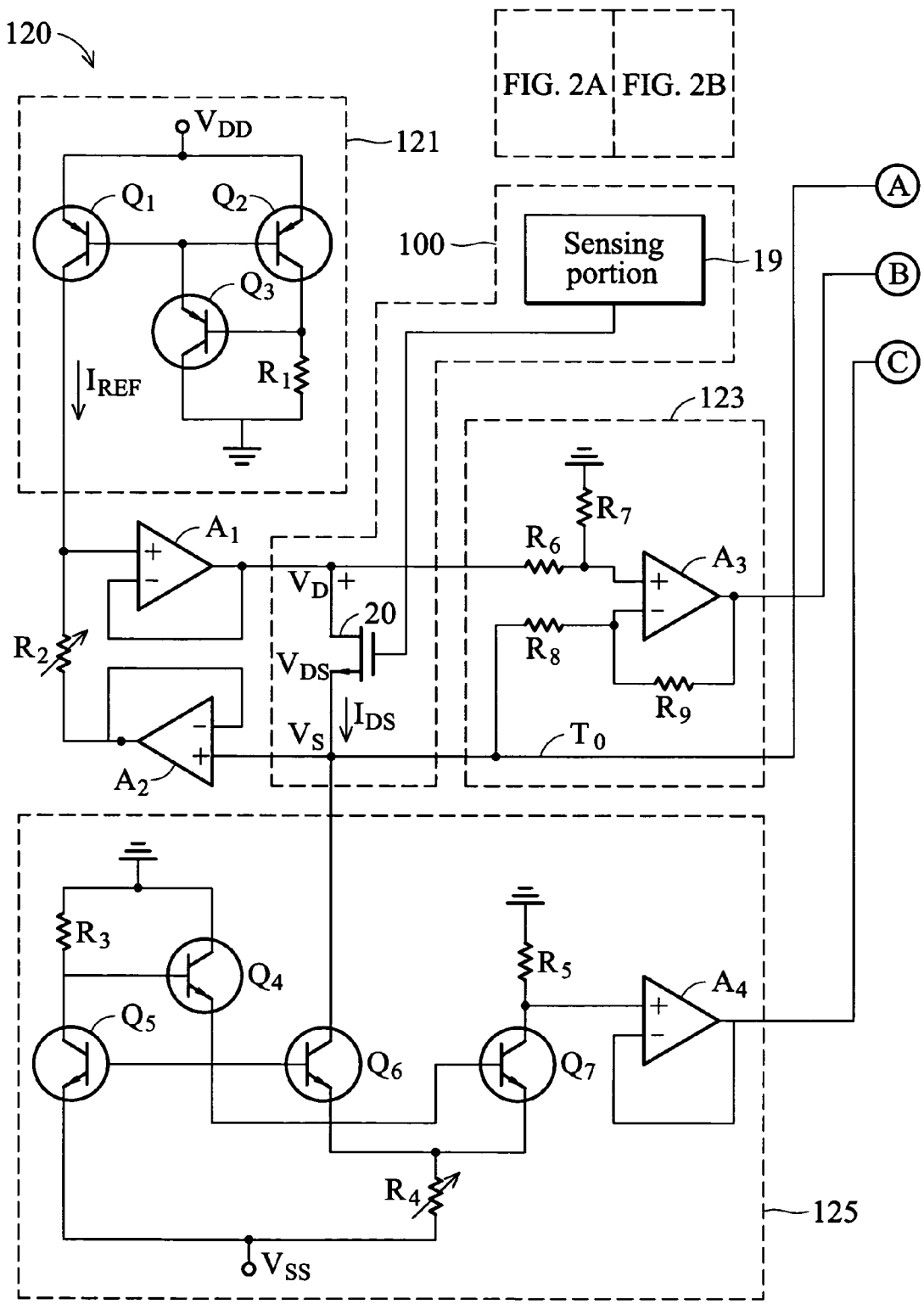
FIGS. 2A and 2B are an exemplary embodiment of a read circuit.
Figure 2B:
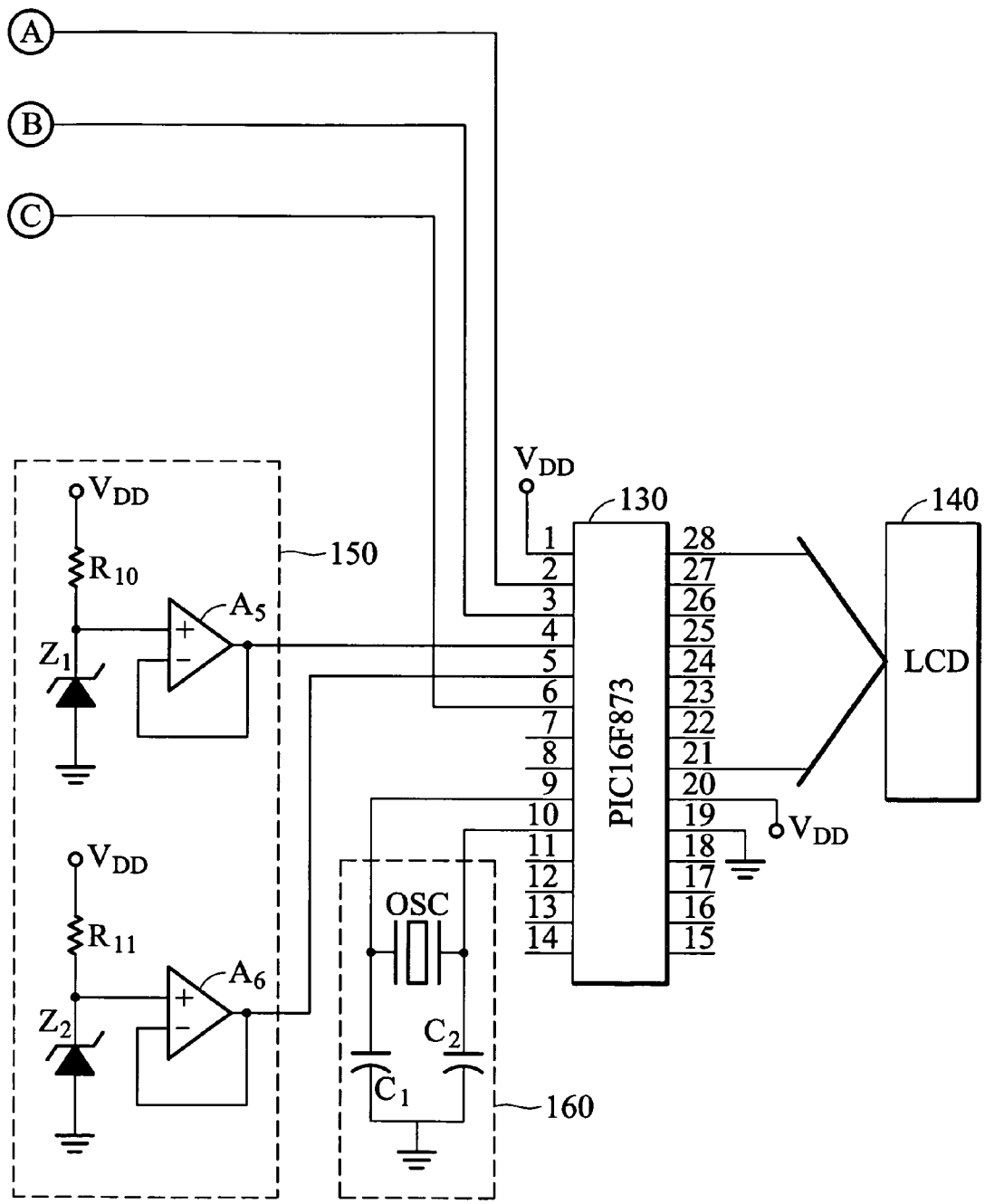

In order to read out pH values of unknown solutions a read circuit is also provided to detect a drain-source voltage and a drain-source current of the ISFET 100 to thereby determine pH values of unknown solutions accordingly. During pH value detection, only the detection film is required to be immersed into the unknown solutions without the MOSFET connected to the detection film. FIGS. 2A and 2B show an exemplary embodiment of a read circuit. Read circuit 200 includes a detection circuit 120, a processing unit 130, a liquid crystal display 140, a reference voltage generation module 150 and an oscillation signal generation module 160.

The detection circuit 120 detects the drain-source voltage $V_{DS}$ and drain-source current $I_{DS}$ of an extended gate ISFET (called EGFET hereinafter) 100. The detection circuit 120 includes a current mirror 121, a first operational amplifier $A_1$, a resistor $R_2$, a second operational amplifier $A_2$, a drain-source voltage detection module 123 and a drain-source current detection module 125.

The current mirror 121 includes three bipolar junction transistors $Q_1 \sim Q_3$ and a resistor $R_2$, and provides a reference current $I_{REF}$ for the detection circuit 120. The transistor $Q_1$ includes a first terminal coupled to a power voltage $V_{DD}$, a second terminal coupled to a non-inversion input terminal of the operational amplifier $A_1$, and a control terminal coupled to a control terminal of the transistor $Q_2$. The transistor $Q_2$ includes a first terminal coupled to the power voltage $V_{DD}$, a second terminal coupled to the resistor $R_1$, and a control terminal coupled to the control terminal of the transistor $Q_1$.

The transistor $Q_3$ includes a first terminal coupled to the control terminals of the transistors $Q_1$ and $Q_2$, a second terminal coupled to a ground voltage, and a control terminal coupled to the resistor $R_2$ and the second terminal of the transistor $Q_2$. The resistor $R_1$ includes a first end coupled to the ground voltage and a second end coupled to a second terminal of the transistor $Q_1$ and the control terminal of the transistor $Q_2$. For example, the resistor $R_2$ can be a variable resistor to adjust the drain-source voltage $V_{DS}$ within 0.0~1.0V, and the current mirror 121 is a constant current source. Further, the current mirror 121 and the resistor R2 combine a constant voltage source to generate a required voltage $V_{DS}$ to control the EGFET 100. The first and second operational amplifiers $A_1$ and $A_2$ constitute a source follower to prevent a loading effect, and the desired voltage $V_D$ at the drain terminal of the EGFET 100 is obtained by the source voltage $V_S$ and the loop constituted by the operational amplifiers $A_1$ and $A_2$ and the resistor $R_2$.

The operational amplifier $A_1$ includes a non-inversion input terminal coupled to second terminal of the operational amplifier $A_2$ and the resistor $R_2$, an output terminal coupled to the drain terminal of the transistor 20, and an inversion input terminal coupled to the output terminal thereof. The operational amplifier $A_2$ includes a non-inversion input terminal coupled to the drain terminal of the transistor 20, an output terminal coupled to the resistor $R_2$, and an inversion terminal coupled to the output terminal thereof.

The drain-source voltage detection module 123 is coupled to the source terminal of the EGFET 100 to detect the drain-source voltage $V_{DS}$ of the EGFET 100. As shown, the drain-source voltage detection module 123 includes an operational amplifier $A_3$ and resistors $R_6 \sim R_9$. For example, the resistors $R_6 \sim R_9$ can be the same, such that the output voltage of the operational amplifier is equal to $V_D \sim V_S$, namely, the drain-source voltage $V_{DS}$. The resistor $R_6$ includes a first end coupled to the non-inversion input terminal of the operational amplifier $A_3$ and the resistor $R_7$, and a second end coupled to the output terminal of the operational amplifier $A_1$ and the drain terminal of the transistor 20. The resistor R8 includes a first end coupled to the non-inversion input terminal of the operational amplifier $A_2$ and the source terminal of the transistor 20, and a second end coupled to the inversion input terminal of the operational amplifier $A_3$ and the resistor $R_9$. The resistor $R_9$ is coupled between the second end of the resistor $R_8$ and the output terminal of the operational amplifier $A_3$.

The drain-source current detection module 125 is coupled to the EGFET 100 to detect the drain-source current of the EGFET 100. The drain-source current detection module 125 includes a Widlar current source, an operational amplifier A4 and a resistor $R_5$. The Wildar current source includes four transistors $Q_4 \sim Q_7$ and two resistors $R_3$ and $R_4$ to control and limit the drain current $I_D$. The resistor $R_4$ can be a variable resistor to adjust the current $I_{DS}$, and the transistor $Q_7$, the resistor $R_5$ and the operational amplifier $A_4$ constitute a sub-detection unit to detect the current $I_{DS}$.

The transistor $Q_4$ includes a first terminal coupled to the ground voltage, a second terminal coupled to the control terminal of the transistor $Q_2$ and a control terminal coupled to a first end of the resistor $R_3$, and a second end of the resistor $R_3$ is coupled to the ground voltage. Transistor $Q_5$ includes a first terminal coupled to the first end of the resistor $R_3$ and the control terminal of the transistor $Q_4$, a control terminal coupled to the control terminal of the transistor $Q_6$, and a second terminal coupled to the power voltage Vss. The transistor $Q_6$ includes a first terminal coupled source terminal of the transistor 20, a control terminal coupled to control terminal of the transistor Q5, and a second terminal coupled to a first end of the fourth resistor $R_4$, and a second end of the fourth resistor $R_4$ is coupled to the power voltage Vss. The transistor $Q_7$ includes a first terminal coupled to the first end of the resistor $R_5$, a control terminal coupled to the control terminal of the transistor $Q_4$, and a second terminal coupled to the first end of the resistor $R_4$. The operational amplifier $A_4$ includes a non-inversion input terminal coupled to the first end of the resistor $R_5$ and the first terminal of the transistor $Q_1$, and an inversion input terminal coupled to an output terminal thereof. The output terminals of the operational amplifiers $A_3$ and $A_4$ and the source terminal of the transistor 20 are coupled to the input terminals of the processing unit 130 respectively.

The reference voltage generation module 150 includes two operational amplifiers $A_5$ and $A_6$, two zener diodes $Z_1$ and $Z_2$ and resistors $R_{10}$ and $R_{11}$. The zener diodes $Z_1$ and $Z_2$ provide stable voltages to the processing unit 130 through the operational amplifiers $A_5$ and $A_6$, such that the processing unit 130 can potentially prevent source noise and reduce fluctuation errors.

The oscillation signal generation module 160 includes an oscillator OCS and two capacitors $C_1$ and $C_2$ to provide oscillation signals to the processing unit 130.

The processing unit 130 determines the pH value of unknown solutions according to the detected drain-source voltage $V_{DS}$ and the detected drain-source current $I_{DS}$ via detection circuit 120. The processing unit 130 can be microprocessor PIC16F873 manufactured by Microchip. The liquid crystal display 140 is coupled to the processing unit 130 to display the determined pH value of unknown solutions.

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A fabrication method for ion sensitive field effect transistors (ISFETs) with a $SnO_2$ extended gate, comprising:

providing a substrate;

forming a $SnO_2$ detection film on the substrate by sol-gel technology to serve as an extended gate;

electrically connecting the $SnO_2$ detection film with a conductive wire;

forming an insulating layer on the surface of the ISFET but exposing part of the $SnO_2$ detection film and part of the conductive wire; and electrically connecting the exposed conductive wire and a gate terminal of a MOS transistor.

2. The fabrication method as claimed in claim 1, wherein the insulating layer comprises epoxy resin.

3. The fabrication method as claimed in claim 1, wherein forming the $SnO_2$ detection film on the substrate comprises:

dissolving $SnCl_2$ powder by ethanol to form a mixed solution;

placing the mixed solution for a first predetermined duration to form a light yellow color mixed solution;

coating the light yellow color mixed solution on the substrate; and heating the substrate to a first predetermined temperature for a second predetermined duration.

4. The fabrication method as claimed in claim 3, wherein the concentration of the solution comprising $SnCl_2$ and ethanol is about 0.37M.

5. The fabrication method as claimed in claim 4, wherein the first predetermined temperature is 350° C.

6. The fabrication method as claimed in claim 4, wherein the second predetermined duration is 1 hour.

7. The fabrication method as claimed in claim 1, further comprising rinsing the substrate for a third predetermined duration by propyl alcohol, isopropanol and deionization water (DI water) respectively before forming the $SnO_2$ detection film.

8. The fabrication method as claimed in claim 7, wherein third predetermined duration is 20 minutes.

9. The fabrication method as claimed in claim 2, wherein connecting the $SnO_2$ detection film on substrate with the conductive wire comprises:

rinsing the substrate with the $SnO_2$ detection film by DI water;

fixing a first terminal of the conductive wire to the $SnO_2$ detection film by silver paste; and heating the substrate to a second predetermined temperature for a fourth predetermined duration.

10. The fabrication method as claimed in claim 9, wherein the fourth predetermined duration is 10 minutes.

11. The fabrication method as claimed in claim 9, wherein forming an insulating layer on the surface of the ISFET comprises:

installing the conductive wire through a capillary;

packaging the substrate, the $SnO_2$ detection film, the conductive wire and capillary by the insulating layer but exposing part of the $SnO_2$ detection film, part of the conductive wire and part of the capillary; and heating the substrate to the second predetermined temperature for a fifth predetermined duration.

12. The fabrication method as claimed in claim 11, wherein the second predetermined temperature is 120° C.

13. The fabrication method as claimed in claim 11, wherein the fifth predetermined duration is 20 minutes.

* * * * *